March 31, 1964 O. O. DUNHAM Plant Pat. 2,388
CHRYSANTHEMUM PLANT
Filed Sept. 7, 1962
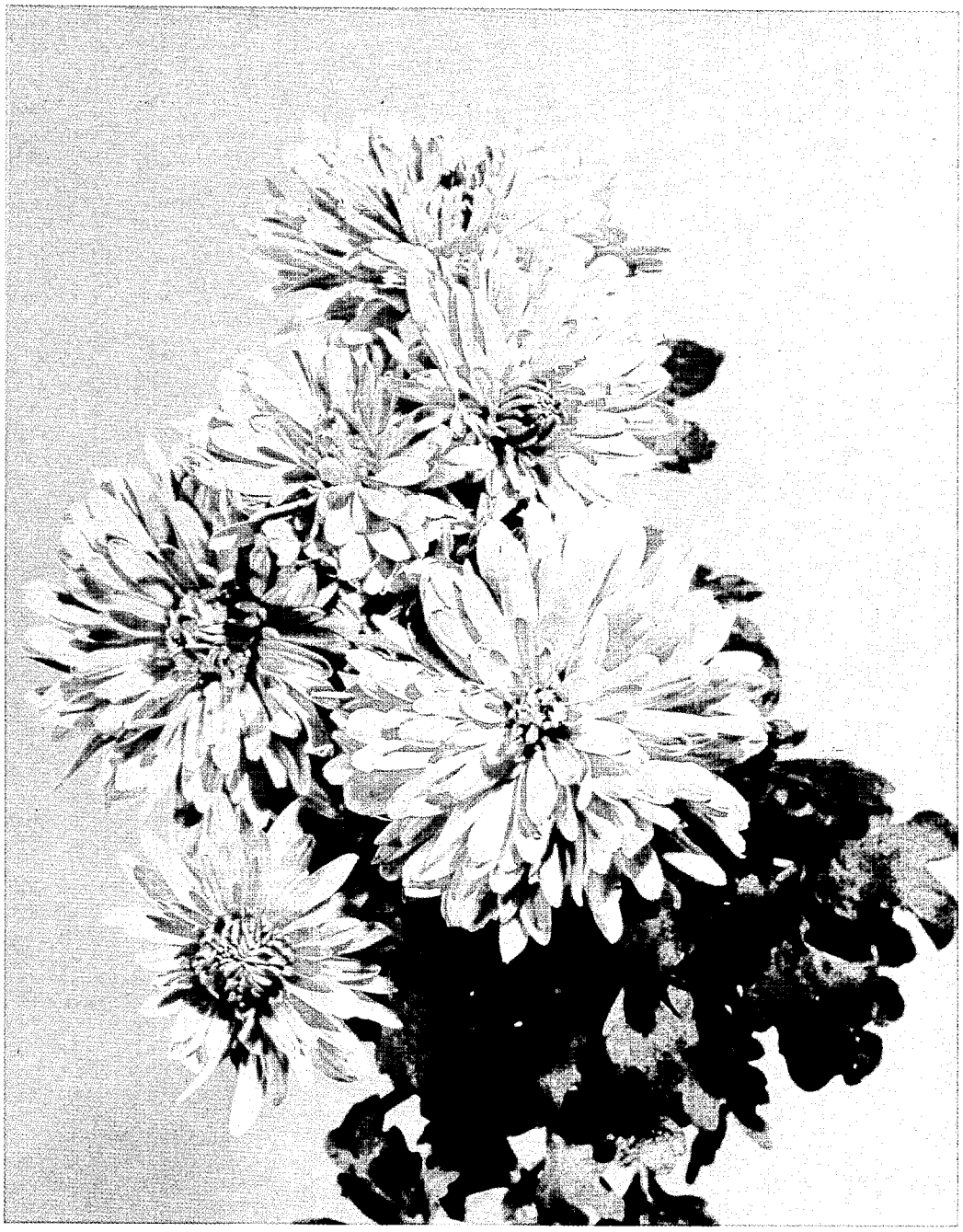
Inventor
O. O. Dunham
by Robb & Robb
Attorneys United States Patent Office Plant Pat. 2,388
Patented Mar. 31, 1964

2,388
CHRYSANTHEMUM PLANT
Orville O. Dunham, Rte. 4, Niles, Mich.
Filed Sept. 7, 1962, Ser. No. 222,251
1 Claim. (Cl. Plt.—81)

My present invention comprises a new and distinct variety of chrysanthemum plant which is the result of crossing the variety "Cameo" an unpatented variety of my own introduction, with a further variety of my own introduction, likewise unpatented and known as "Coquette."

The object of this invention has been to produce a new variety of *Chrysanthemum indicum* which derives the color of its blooms from the pollen parent and its plant habit from the seed parent, with the retaining of other desirable characteristics of both an improvement on the same, with the cushion natural dwarf habit of growth being primarily of advantage and retained hereby.

I have had an opportunity to observe many different types of chrysanthemums and as a hydridizer, have conducted an intensive program of development to provide new and distinct varieties, of which the instant variety is a product and results from careful selection and cross breeding of various chrysanthemum plants basically those from the so-called American Garden Mums and endeavoring to produce distinct and better varieties of garden mums with novelty characteristics that make them different and better from prior garden mums now in commerce.

The result of the hydridization previously referred to has been to produce my present new and distinct variety of chrysanthemum characterized by the deep pink tinted with strong purplish pink color of its blooms, natural dwarf cushion mound form of growth, simultaneous bursting into flower of its blooms to cover substantially all the foliage, the attractive color of its foliage during growth and its midseason profuse and continuous blooming habit.

More specifically the blooms of my new variety are of the deep pink tinted with strong purplish pink color (Nickerson Color Fan published by the Munsell Color Company), the blooms having the lighter outer color with darkening to the strong purplish pink at the center. As grown in the vicinity of Niles, Michigan, in uniform culture, plants of my new variety grow to an average height of 12" to 14" in the mound form previously mentioned.

My new variety derives a number of characteristics from both parents, but better characteristics than either separately and my new variety differs from both of its parents and from other known varieties in many respects.

My new variety derives its general color tonality from the pollen parent "Coquette," but I note that the color is even more decided in the instant variety. The seed parent "Cameo" apparently has transmitted to the seedling hereof the plant habit of substantially uniform mound shape, but the foliage itself seems to be a product of the crossing of both varieties.

Under the conditions of culture previously mentioned, which have been undertaken in the region of Niles, Michigan, plants of my new variety have grown very vigorously with profuse foliage, in uniform mound shape perhaps slightly more dwarf than the seed parent "Cameo."

My new variety when grown in the region of Niles, Michigan, blooms from late September until a killing frost continuously there being a profuse number of blooms on each plant.

My new variety has been asexually reproduced by cuttings in the vicinity of Niles, Michigan, with the observations made herein as a basis during late September and early October.

My new variety has been found to retain its distinctive characteristics through successive asexual reproduction.

The accompanying drawing forming a part hereof shows a typical plant of my new variety of chrysanthemum in a color illustration which is as reasonably accurate as is possible to make in color illustrations of this nature.

The following is a detailed description of my new variety of chrysanthemum plant, the color references being to the Nickerson Color Fan published by the Munsell Color Company:

*Description*

Parentage: Seedling.
*Seed parents.*—"Cameo" (unpatented).
*Pollen parent.*—"Coquette" (unpatented).
Classification: Botanic—*Chrysanthemum indicum.*

*Flower*

Blooming habit: Blooms profusely and continuously from late September until a killing frost and bursts into bloom in what appears to be an all over display.

Bud:
*Size.*—Small.
*Form.*—Short with flat top.
Not affected substantially by hot or wet weather.
*Color.*—When petals begin to unfurl: 10 RP 6/12. When half blown: Inside of petals—10 RP 6/12. Reverse of petals—10 Rp 6/12.
*Sepals.*—Of no consequence.
*Calyx.* — Shape — funnel. Size—small. Aspect—hairy.
*Peduncle.* — Length — medium. Aspect — rough. Strength—stiff, erect.
Bud opens well and is not affected by adverse conditions.

Bloom:
*Size.*—Small. Average size when fully expanded about 2".
*Borne.*—In clusters and flat.
*Stems.*—Short, strong.
*Form.*—When first open—flat. Permanence—retains its form to the end.
*Petalage.*—Double. Innumerable petals under normal conditions.
*Color.*—Center of flower—10 RP 6/12 tinted with 5 RP 7/9. Outer petals—10 RP 6/12 tinted with 5 RP 7/9. Base of petals—10 RP 6/12 tinted with 5 RP 7/9. Inside of petals—10 RP 6/12 tinted with 5 RP 7/9. Reverse of petals—10 RP 6/12 tinted with 5 RP 7/9. General tonality from a distance—10 RP 6/12 tinted with 5 RP 7/9.
*Discoloration.*—General tonality at end of: First week—retains same color as above. Second week—about the same color as above. Third week—lightens slightly.

Petals:
*Texture.*—Thin. Not affected by wet or hot weather.
*Appearance.*—Inside—velvety. Outside—satiny.
*Form.*—Oval.
*Arrangement.*—Imbricated.
*Persistence.*—Hang on and dry.
*Fragrance.*—None.
*Lastingness.*—On the plant—long. Cut flower—long.

Genital organs:
*Stamens, anthers.*—Small, few. Arrangement—regular around styles.
*Stamens, filaments.*—Medium.
*Styles.*—Columnar, short.
*Ovaries.*—All enclosed in calyx.

Plant:
*Form.*—Bush.
*Growth.*—Vigorous, dwarf, branching, and compact.

Foliage:
*Size.*—Medium.

*Quantity.*—Abundant.
*Old foliage.*—Upper side—10 GY 4/5. Under side —10 GY 5/8.
*Shape.*—Three lobed.
*Texture.*—Upper side—smooth. Under side—velvety. Ribs and veins—ordinary.
*Edge.*—Smooth.
*Stipules.*—Short.

I claim:

A new and distinct variety of chrysanthemum plant substantially as herein disclosed, characterized as to novelty by the deep pink tinted with strong purplish pink color of its blooms, the natural dwarf cushion mound form of growth, simultaneous bursting into flower of its blooms to cover substantially all the foliage, the attractive color of the foliage during growth and its midseason, profuse and continuous blooming habit.

No references cited.